United States Patent
Thibault et al.

(10) Patent No.: US 9,261,467 B2
(45) Date of Patent: Feb. 16, 2016

(54) SYSTEM AND METHOD OF ITERATIVE IMAGE RECONSTRUCTION FOR COMPUTED TOMOGRAPHY

(71) Applicants: General Electric Company, Schenectady, NY (US); University of Notre Dame du Lac, Notre Dame, IN (US); Purdue Research Foundation, West Lafayette, IN (US)

(72) Inventors: Jean-Baptiste Thibault, Milwaukee, WI (US); Xue Rui, Clifton Park, NY (US); Somesh Srivastava, Waukesha, WI (US); Ken David Sauer, South Bend, IN (US); Lin Fu, Niskayuna, NY (US); Charles Addison Bouman, Jr., West Lafayette, IN (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 291 days.

(21) Appl. No.: 13/918,215

(22) Filed: Jun. 14, 2013

(65) Prior Publication Data

US 2014/0369463 A1 Dec. 18, 2014

(51) Int. Cl.
| | |
|---|---|
| G06K 9/00 | (2006.01) |
| G01N 23/04 | (2006.01) |
| A61B 6/03 | (2006.01) |
| A61B 6/00 | (2006.01) |
| G06T 11/00 | (2006.01) |

(52) U.S. Cl.
CPC .............. *G01N 23/046* (2013.01); *A61B 6/032* (2013.01); *A61B 6/5205* (2013.01); *G06T 11/006* (2013.01); *G01N 2223/1016* (2013.01); *G01N 2223/419* (2013.01); *G06T 2211/424* (2013.01)

(58) Field of Classification Search
None
See application file for complete search history.

(56) References Cited

U.S. PATENT DOCUMENTS

2012/0294414 A1* 11/2012 Koehler ..................... 378/16

OTHER PUBLICATIONS

Wang, Jing, et al. "Penalized weighted least-squares approach to sinogram noise reduction and image reconstruction for low-dose X-ray computed tomography." Medical Imaging, IEEE Transactions on 25.10 (2006): 1272-1283.*

Sauer et al., "A Local Update Strategy for Iterative Reconstruction from Projections," IEEE Transactions on Signal Processing, vol. 41, No. 2, Feb. 1993, pp. 534-548.

(Continued)

*Primary Examiner* — Nirav G Patel
(74) *Attorney, Agent, or Firm* — Lucas Divine; General Electric Company (57) ABSTRACT

A system and method include acquisition of projection data from a scanned object, the set of projection data comprising a plurality of projection measurements. The system and method also include calculation of a set of modified statistical weights from the projection data, wherein a respective modified statistical weight of the set of modified statistical weights comprises a deviation from an inverse variance of a corresponding projection measurement of the projection data. The system and method further include reconstruction of an image of the scanned object using the set of modified statistical weights as coefficients in an iterative reconstruction algorithm.

21 Claims, 7 Drawing Sheets

(56) References Cited

OTHER PUBLICATIONS

Thibault et al., "A three-dimensional statistical approach to improved image quality for multislice helical CT," Medical Physics, vol. 34, No. 11, Nov. 2007, pp. 4526-4544.

Thibault et al., "A Recursive Filter for Noise Reduction in Statistical Iterative Tomographic Imaging," Proceedings of the SPIE-IS&T Symposium on Electronic Imaging Science and Technology—Computational Imaging, San Jose, California, Jan. 15-19, 2006, vol. 6065, pp. 60650X-1-60650X-10.

* cited by examiner

SYSTEM AND METHOD OF ITERATIVE IMAGE RECONSTRUCTION FOR COMPUTED TOMOGRAPHY

BACKGROUND OF THE INVENTION

Embodiments of the invention relate generally to diagnostic imaging and, more particularly, to a system and method of iterative image reconstruction for computed tomography.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction. Alternatively, x-ray detectors may use a direct conversion detector, such as a CZT detector, in lieu of a scintillator.

CT systems typically use analytical algorithms such as a filtered back-projection algorithm to reconstruct images from the acquired image data. Alternatively, an iterative technique may be used for reconstruction to improve image quality. For example, a model-based iterative reconstruction algorithm may be used to estimate an image based on pre-determined models of the CT system, the acquired projection data, and the reconstructed image such that the reconstructed image best fits the image data.

A typical model-based iterative reconstruction framework reconstructs an image of the scanned object from projection data according to the general equation:

$$\hat{x} = \underset{x \in \Omega}{\mathrm{argmin}}\{D(y - F(x)) + U(x)\}, \quad (\text{Eqn. 1})$$

where x is the discrete vector of reconstructed values (for instance a 3D image), y is the discrete vector of measurement values (e.g., a CT projection dataset), $\Omega$ is a constraint set for the space of solutions (e.g., the set of non-negative solutions in x), $D(\cdot)$ is an convex scalar valued function (e.g., a log-likelihood function used as a metric for relating the measurement vector y to the reconstructed vector x), $U(\cdot)$ is a scalar value regularization term (e.g., a function that penalizes local differences between voxel elements in x), and $F(\cdot)$ is a transformation of the image space x in a manner similar to the scanning system (e.g., a CT scanner).

An iterative optimization algorithm is used to solve Eqn. 1. The quantity F(x) may be modeled as a discretized linear relationship of the form F(x)=Ax, where A is the system matrix for the forward projection of x according to the imaging system. The negative log-likelihood function $D(\cdot)$ is derived from the Poisson distribution of the measurements y via a Taylor series expansion to arrive at a quadratic component of the overall regularized cost function or Maximum A Posteriori (MAP) estimation:

$$\hat{x} = \underset{x \geq 0}{\mathrm{argmin}}\left\{\frac{1}{2}(y - Ax)W(y - Ax) + U(x)\right\}, \quad (\text{Eqn. 2})$$

where W is a diagonal conventional statistical weighting matrix whose elements are approximately inversely proportional to the variance in the projection measurements y over the range of weights within the matrix.

The elements of the conventional statistical weighting matrix W are used to control the influence of each individual projection ray during the iterative image reconstruction. Statistical weighting plays a large factor in the quality of the reconstructed results and defines ones of the unique properties of model-based iterative reconstruction relative to standard analytical reconstruction methods such as filtered back-projection.

Conventional statistical weights are calculated from the inverse variance in the actual projection data. In the absence of electronic noise, the inverse variance in projection measurements is calculated to be proportional to the photon count $\lambda$:

$$w_i \propto \frac{1}{\sigma_{y_i}^2}, \quad (\text{Eqn. 3})$$

where y is the projection data. The value a may be calculated using the raw photon count measurements X alone or in combination with the known electronic noise in the data acquisition system.

While conventional statistical weighting techniques such as those described above may be used to reduce image noise, the coefficients used in these standard models are highly spatially-variant for reconstructing complex objects. The resulting large dynamic range in the weights can slow down the convergence of the iterative optimization algorithm and be associated with image artifacts. For instance, in the case of a data inconsistency between the model used for reconstruction and the real projection data, such as when the scanned object moves during the scan and the model assumes no motion is present, large local changes in the conventional statistical weights may increase the magnitude of image artifacts.

Statistical weights are also associated with image texture by controlling the correlation in the noise of the reconstructed image pixels. For medical imaging in particular, image texture is an important consideration when attempting to represent tissue as realistically as possible.

Therefore, it would be desirable to design a system and method of iterative image reconstruction that overcomes the aforementioned drawbacks of conventional statistical weighting techniques.

BRIEF DESCRIPTION OF THE INVENTION

In accordance with one aspect of the invention, a non-transitory computer readable storage medium has stored thereon a computer program comprising instructions, which, when executed by a computer, cause the computer to acquire projection data from a scanned object, the set of projection data comprising a plurality of projection measurements. The instructions further cause the computer to calculate a set of modified statistical weights from the projection data, wherein a respective modified statistical weight of the set of modified statistical weights comprises a deviation from an inverse variance of a corresponding projection measurement of the projection data. The instructions also cause the computer to reconstruct an image of the scanned object using the set of modified statistical weights as coefficients in an iterative reconstruction algorithm.

In accordance with another aspect of the invention, a method includes acquiring a projection dataset from an object using a medical imaging device, the projection dataset comprising a plurality of projection measurements representing attenuation of x-rays by the object. The method also includes generating a modified statistical weighting matrix comprising a plurality of weights that deviate from an inverse variance in the plurality of projection measurements and reconstructing an image of the object based on the modified statistical weighting matrix.

In accordance with another aspect of the invention, an imaging system includes a rotatable gantry having an opening for receiving an object to be scanned and an x-ray source coupled to the rotatable gantry and configured to project x-rays through the opening. A generator is configured to energize the x-ray source to an energy level to generate x-rays corresponding to the energy level and a detector having pixels therein, the detector attached to the rotatable gantry and positioned to receive x-rays projected from the x-ray source. The imaging system also includes a computer programmed to access a CT projection dataset acquired from the object over a period of data acquisition, calculate a set of modified statistical weights for an iterative reconstruction algorithm using a scalar parameter tuned to differentiate projection rays of the CT projection dataset having differing attenuation values, and iteratively reconstruct the CT projection dataset using the set of modified statistical weights as coefficients in the iterative reconstruction algorithm.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

The operating environment of embodiments of the invention is described with respect to a sixty-four-slice computed tomography (CT) system. However, it will be appreciated by those skilled in the art that embodiments of the invention are equally applicable for use with other multi-slice configurations. In addition, while embodiments of the invention are described with respect to iterative reconstruction techniques for use with CT systems, one skilled in the art will recognize that the concepts set forth herein are not limited to CT and can be applied to iterative reconstruction techniques used with other imaging modalities in both the medical field and non-medical field, such as, for example, an x-ray system, a PET system, a SPECT system, an MR system, or any combination thereof. Moreover, embodiments of the invention will be described with respect to the detection and conversion of x-rays. However, one skilled in the art will further appreciate that embodiments of the invention are equally applicable for the detection and conversion of other high frequency electromagnetic energy. Embodiments of the invention will be described with respect to a "third generation" CT scanner, but are equally applicable with other CT systems.

Figure 1:
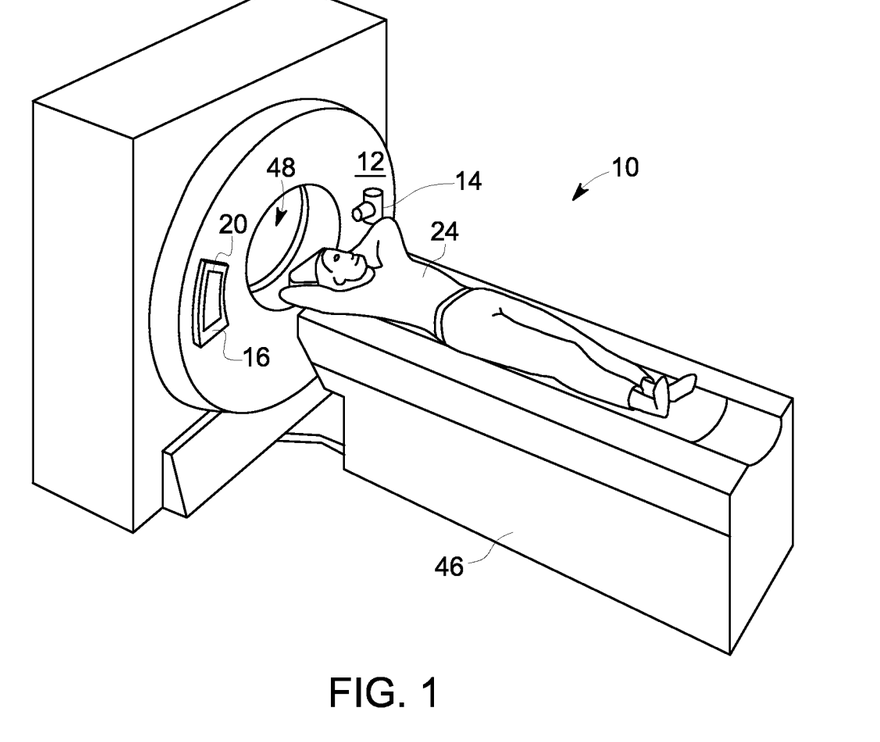
FIG. 1 is a pictorial view of a CT imaging system.
Figure 2:
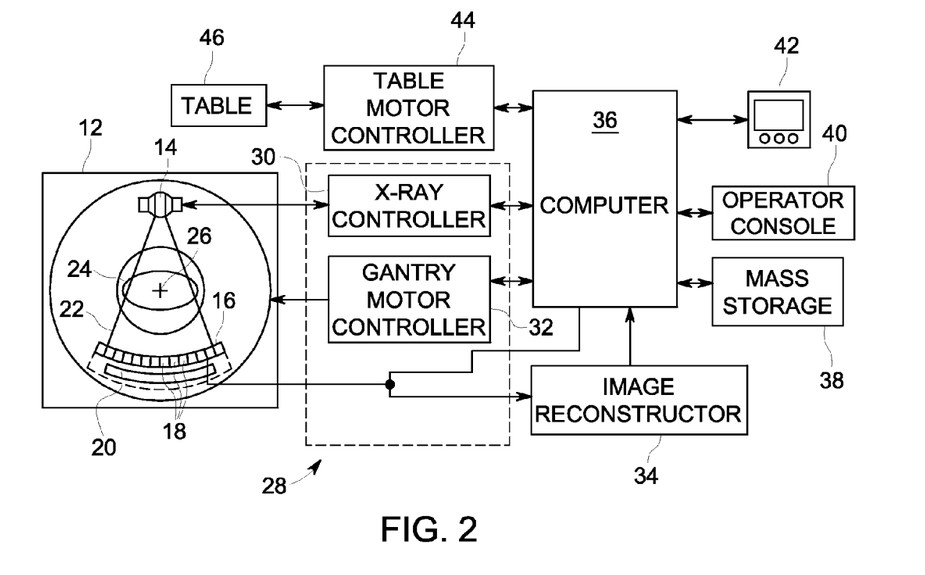
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays 16 that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor or computer processor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
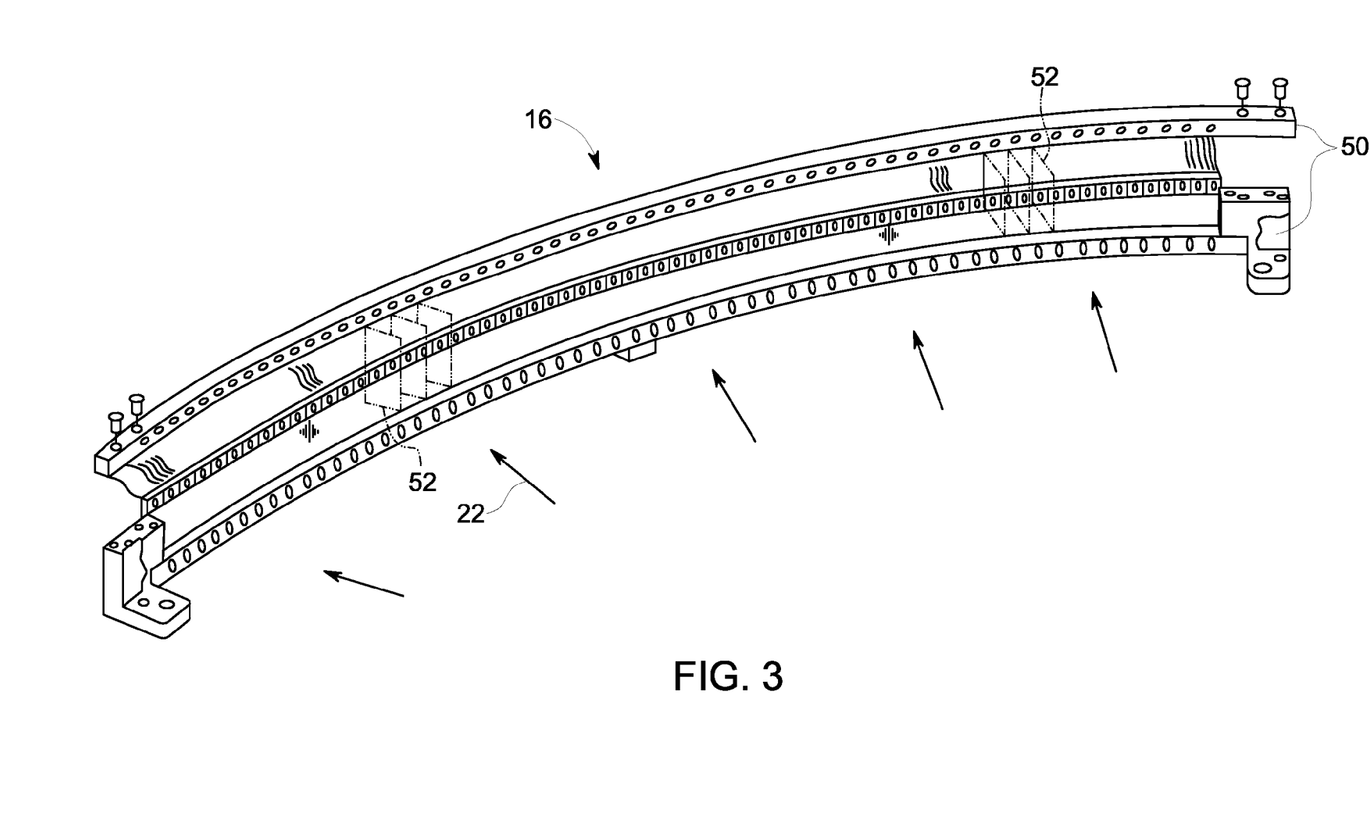
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
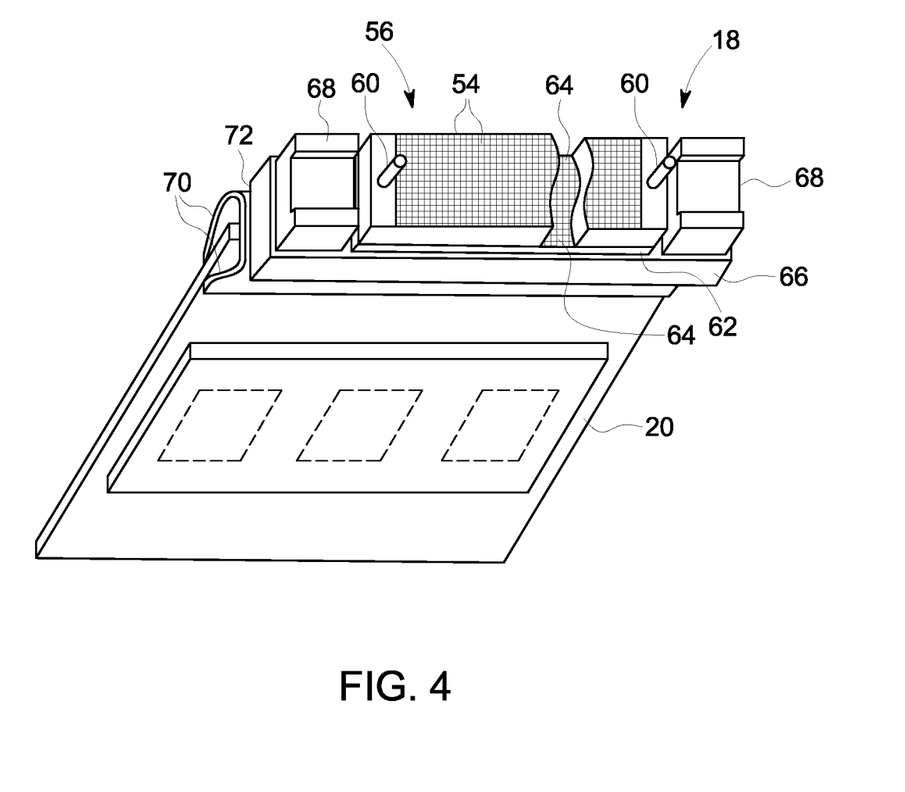
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

Figure 5:
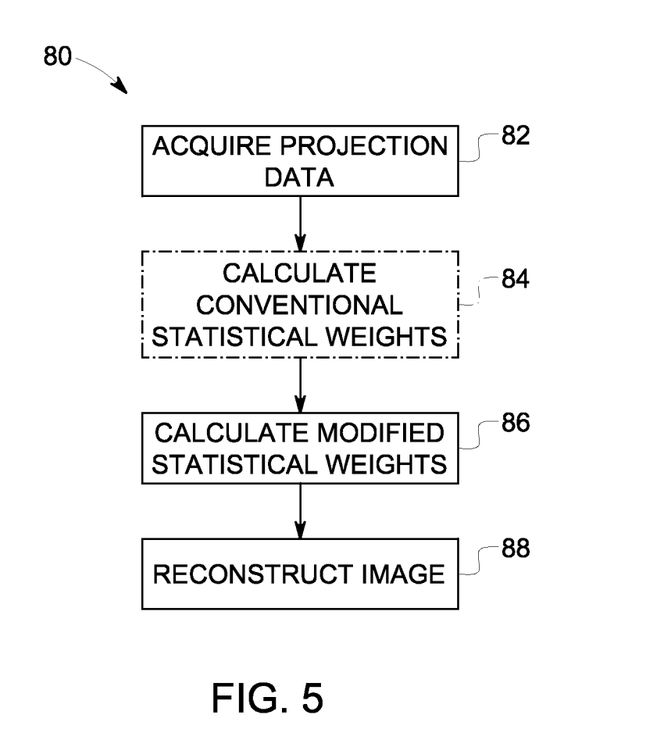
FIG. 5 is a flowchart illustrating a technique for reconstructing an image according to embodiments of the invention.

Referring now to FIG. 5, a model-based iterative reconstruction technique 80 is set forth according to an embodiment of the invention. As described in detail below, technique 80 calculates modified statistical weights that represent a deviation from conventional statistical weights, which are calculated based on the inverse variance in the projection measurements. The modified statistical weights are used in the iterative reconstruction to achieve desired properties in the reconstructed image.

Technique 80 begins by acquiring projection data at step 82 over a given time window or period of data acquisition. During data acquisition, each voxel $x_j$ in the image volume x is illuminated by or exposed to an x-ray source, such as x-ray source 14 of FIG. 1. Projection data y, which represents the projection line integrals for the attenuation of x-rays by the scanned object, is obtained from the raw photon count measurements $\lambda$.

At optional step 84 (shown in phantom), technique 80 calculates conventional statistical weights for use in the iterative reconstruction. As used herein, W represents a conventional statistical weighting matrix used to weight a vector quantity of the discrepancy between the projection measurement data and a forward projection of the reconstructed image, such as (y−Ax). Variables $w_i$ represent elements i of the conventional statistical weighting matrix W.

As described above, conventional statistical weighting matrix W and the elements $w_i$ thereof are calculated to represent the inverse variance of the projection measurements and may be calculated using a technique that accounts for changes in the inverse variance of a random variable via the pre-processing chain resulting in the projection data y, using a technique that models energy-dependent behavior of the detection system, or another known technique.

At step 86, technique 80 calculates a matrix of modified statistical weights $\tilde{W}$ using a transformation function $G(\cdot)$. As used herein variable $\tilde{w}_i$ represents element i of the modified statistical weighting matrix $\tilde{W}$. In one embodiment, transformation function $G(\cdot)$ is defined as a function of the conventional statistical weighting matrix W calculated at step 84:

$$\tilde{W} = G(W) \quad \text{(Eqn. 4)}.$$

In alternative embodiments, the modified statistical weights matrix $\tilde{W}$ is calculated directly from projection measurements y, as described in more detail below.

The modified reconstruction operator is then determined according to:

$$\hat{x} = \operatorname*{argmin}_{x \geq 0} \left\{ \frac{1}{2}(y - Ax)\tilde{W}(y - Ax) + U(x) \right\}. \quad \text{(Eqn. 5)}$$

As described in detail below, the transformation function $G(\cdot)$ is an affine or nonlinear function that effectively modifies the dynamic range of the conventional statistical weights matrix W, either locally or globally or both, in order to achieve desired objectives of the reconstruction, according to various embodiments. As used herein, the phrase "global dynamic range" refers to the ratio of the maximum and minimum statistical weights of the conventional statistical weights matrix W. "Local dynamic range" refers to a ratio of the maximum and minimum statistical weights within a subset of the conventional statistical weights matrix W, for example weights below a predetermined threshold.

As one example, transformation function $G(\cdot)$ may be defined to achieve reduction in the overall dynamic range of the conventional statistical weights in order to reduce image artifacts due to motion or other data inconsistencies, or to speed up convergence. Alternatively, transformation function $G(\cdot)$ may be defined to increase the local difference between statistical weights associated with projection rays of strong attenuation and statistical weights associated with other projection rays of lower attenuation in order to further reduce artifacts due to metal or other dense objects relative to conventional statistical weighting.

Following the calculation of the modified statistical weights at step 86, technique 80 reconstructs an image of the scanned object at step 88 using the modified statistical weights in accordance with the modified iterative reconstruction operator set forth in Eqn. 5.

According to a first embodiment, transformation function $G(\cdot)$ is a nonlinear function that includes an empirical parameter to control the balance between low statistical weights and high statistical weights to account for the varying Signal-to-Noise Ratios (SNR) in the projection measurements due to the different attenuation paths along different projection rays. In such an embodiment, the elements $\tilde{w}$ of the modified statistical weighting matrix $\tilde{W}$ are calculated according to:

$$\tilde{w}_i = \frac{t}{\sigma_{y_i}(\sigma_{y_i} + t)} = \frac{t}{\frac{1}{\sqrt{w_i}}\left(\frac{1}{\sqrt{w_i}} + t\right)}, \quad \text{(Eqn. 6)}$$

where $\sigma_{y_i}$ is the standard deviation of the projection measurements $y_i$ and t is a scalar parameter that may be tuned to differentiate the high SNR projection rays from the low SNR projection rays.

The presence of high density objects in the scanned object, such as metal objects for example, causes relatively high attenuation of the X-ray beams as they propagate through the subject, thereby resulting in a reconstructed image with artifacts. These artifacts can produce significant dark and bright streaks in the reconstructed image that severely limit the CT assessment of soft tissue and bone structures surrounding the high density objects. The artifacts are due to one or more effects such as beam hardening, poor signal-to-noise ratio, scattered radiation, partial volume effect, aliasing, and object motion. While metal artifacts are improved in conventional model-based iterative reconstruction relative to filtered back projection due to the use of conventional statistical weights in the iterative reconstruction, technique 80 may be used to further reduce metal artifacts by effectively modifying the conventional statistical weights associated with these highly attenuated rays using a nonlinear transformation function, in accordance with another embodiment of the invention.

Referring again to FIG. 5, technique 80 calculates the modified statistical weights at step 86 using a soft threshold in the projection value $p_t$ for modifying the conventional statistical weights associated with these highly attenuated rays. A factor $\alpha$ is calculated for each projection ray based on its value y according to:

$$\alpha = \exp(p_t - y) \quad \text{(Eqn. 7)}.$$

The elements $\tilde{w}_i$ of the modified statistical weighting matrix $\tilde{W}$ are then calculated according to:

$$\tilde{w}_i = G(w_i) = \frac{w_i}{1 + \frac{c}{\alpha} e^{-\alpha}}, \quad \text{(Eqn. 8)}$$

where c is a parameter that controls the reduction of the conventional statistical weights for the highly attenuated rays. The threshold $p_t$ in this model is used as a parameter in the nonlinear transformation function to allow a smooth transition between the modified statistical weights $\tilde{w}_i$ below the chosen threshold and the modified statistical weights $\tilde{w}_i$ above the chosen threshold. At the same time, this nonlinear transformation function has a sharp transition near the threshold, preserving the original, conventional statistical weights below the threshold.

A nonlinear transformation function may also be defined to modify the overall dynamic range of the conventional statistical weights, according to another embodiment. In such an embodiment, the modified statistical weights $\tilde{w}_i$ are calculated by applying a power transformation according to:

$$\tilde{w}_i = G(w_i) = w_i^a \quad \text{(Eqn. 9)}$$

where a is a floating point scalar parameter. When a is defined as greater than 1, such as, for example, a=2 or a=3, the dynamic range in the conventional statistical weights can be increased so as to further reduce artifacts from dense objects, such as metal. Where a is defined as less than 1, the nonlinear transformation function may be used to modify the texture of the reconstructed image. For example, with a=0.5, the modified statistical weights deliver a more isotropic noise covariance across the reconstructed image than conventional statistical weights, thus improving image texture.

In accordance with another embodiment, the power transformation model set forth in Eqn. 9 is combined with the adaptive scaling model of Eqn. 8 as follows:

$$\tilde{w}_i = G(w_i) = \frac{w_i^a}{1 + \frac{c}{\alpha} e^{-\alpha}}. \quad \text{(Eqn. 10)}$$

The nonlinear transformation function of Eqn. 10 may be used to generate modified statistical weights that improve image texture while suppressing metal artifacts.

For flexibility in the image reconstruction, it may be desired to regain the original dynamic range of the conventional statistical weights $w_i$ in a certain range of attenuation values while applying a power transformation in another range of attenuation values. As one example, a power transformation as set forth in Eqn. 9 may be applied with a<1 or a=0.5 to control image texture for high SNR projection rays, while retaining the original dynamic range of the conventional statistical weights $w_i$ for lower SNR projection rays to reduce metal and shading artifacts. In such an embodiment, technique 80 may be configured to apply a nonlinear transformation function at step 86 in which full power is applied below a threshold $p_t$ defined in the projection domain and the original dynamic range of the conventional statistical weights is preserved for projection values over the threshold $p_t$ according to:

$$\tilde{w}_i = G(w_i) = \begin{cases} w_i^a & \text{if } y \le p_t \\ \left(\frac{e^{p_t}}{e^{y_i}}\right)^{1-a} w_i^a & \text{if } y > p_t \end{cases}. \quad \text{(Eqn. 11)}$$

Thus, the nonlinear transformation of Eqn. 11 allows a smooth transition between the two regions of statistical weights. In this embodiment, the ratio of two modified statistical weights in one of the two regions is defined as:

$$\frac{\tilde{w}_1}{\tilde{w}_2} = \begin{cases} \left(\frac{e^{y_2}}{e^{y_1}}\right)^a & \text{if } y \le p_t \\ \left(\frac{e^{y_2}}{e^{y_2}}\right)^{1-a} \left(\frac{w_1}{w_2}\right)^a = \frac{e^{y_2}}{e^{y_1}} & \text{if } y > p_t \end{cases}. \quad \text{(Eqn. 12)}$$

By tuning the threshold $p_t$ used in the nonlinear transformation set forth in Eqn. 11, the number of projection rays that are affected by the power transformation may be adjusted. By choosing the threshold $p_t$ to be in the projection domain, technique 80 is robust across different dose levels, mAs, and kVp, which may vary during the scan or among different scans. As one exemplary embodiment, a may be chosen to be equal to 0.5 to provide a more isotropic noise texture in the reconstructed image while preserving benefits provided by conventional statistical weights.

The nonlinear transformation function set forth in Eqn. 11 partially retains the original dynamic range of the conventional statistical weights, by retaining the original dynamic range of the conventional statistical weights for projection rays above the chosen threshold, $p_t$, and modifying the conventional statistical weights for projection rays below the chosen threshold. According to alternative embodiments, it may be desired to retain the exact dynamic range of the original, conventional statistical weights (i.e., a global dynamic range). The affine transformation function set forth below in Eqn. 13 retains the original global dynamic range of the entire matrix of conventional statistical weights:

$$\tilde{w}_i = G(w_i) = \quad \text{(Eqn. 13)}$$
$$\begin{cases} w_i^a & \text{if } y \le p_t \\ w_t^a + \frac{c}{\left(\frac{e^{p_t}}{e^{p_{max}}}\right)^{1-a} w_{min}^a - w_t^a} \left(\left(\frac{e^{p_t}}{e^{y_i}}\right)^{1-a} w_i^a - w_t^a\right) & \text{if } > p_t \end{cases},$$

where $w_{max}{}^a$ is the maximum of the conventional statistical weights and $w_{min}{}^a$ is the minimum of the conventional statistical weights. The factor c is calculated according to:

$$c = \frac{w_{max}}{w_{min}}. \quad \text{(Eqn. 14)}$$

The threshold statistical weight $w_t$ in Eqn. 13 corresponds to the projection value $p_t$. To retain the global dynamic range of the conventional statistical weights, with $w_{max} \rightarrow w_{max}{}^a$ following application of the affine transformation, the minimum of the modified statistical weights is modified according to $$\left(\frac{e^{p_t}}{e^{p_{max}}}\right)^{1-a} w_{min}^\beta \rightarrow \frac{w_{max}^\beta}{c}.$$

To maintain continuity between the two regions around threshold $p_t$, the modified statistical weights at the threshold remain the same as $w_t{}^a \rightarrow w_t{}^a$. In an exemplary embodiment, a is selected to be 0.5 to achieve relatively isotropic noise covariance for the reconstructed images while maintaining the global dynamic range of the conventional statistical weights.

As explained above, the transformation function set forth in Eqn. 11 preserves the relative dynamic range of statistical weights associated with projection values greater than the threshold $p_t$. In accordance with yet another embodiment of the invention, the ratio of the modified statistical weights for a projection ray above the threshold $p_t$ and a projection ray below the threshold $p_t$ may be controlled using the following nonlinear transformation:

$$\tilde{w}_i = G(w_i) = \begin{cases} \left(\frac{e^{p_t}}{e^{y_i}}\right)(w_i)^a & \text{if } y \leq p_t \\ \left(\frac{e^{p_t}}{e^{y_i}}\right)(w_i)^a & \text{if } y > p_t \end{cases}, \quad \text{(Eqn. 15)}$$

where a is a scalar parameter such as, for example, 0.5, and b and c are scalar exponent parameters selected to control the statistical weights associated with the low end and the high end of the projections, respectively.

The nonlinear transformation of Eqn. 15 separates the modified statistical weights into two different regions, either above or below the chosen projection threshold $p_t$ around a power transformation. The relative dynamic ranges of the two regions of modified statistical weights are controlled by tuning the scalar exponent parameters b and c separately. A single threshold, $p_t$, in the projection domain is again used to divide the modified statistical weights into a first set of modified statistical weights and a second set of modified statistical weights.

In this embodiment, the ratio of a modified statistical weight for a projection ray above the threshold $p_t$ to the modified statistical weight for a projection ray below the threshold $p_t$ is defined as:

$$\frac{\tilde{w}_{1,y>p_t}}{\tilde{w}_{2,y\leq p_t}} = (e^{p_t})^{c-b} \frac{(e^{y_2})^{b+a}}{(e^{y_1})^{c+a}}. \quad \text{(Eqn. 16)}$$

While the transformation described with respect to Eqn. 15 employs a nonlinear transformation to calculate the modified statistical weights in the two different regions, the affine transformation described with respect to Eqn. 13 may alternatively used in this embodiment to retain the original global dynamic range of the conventional statistical weights.

While Equations 8, 9, 10, 11, 13, and 15 are set forth above as calculating the modified statistical weight elements $\tilde{w}_i$ using the conventional statistical weight element $w_i$, one skilled in the art will recognize that these transformation functions may alternatively be calculated directly from the projection data.

Further, technique 80 may use any of the above transformation functions set forth above in Eqns. 6, 8, 9, 10, 11, 13, and 15 either alone, or in combination, to calculate the modified statistical weights $\tilde{w}_i$. In one embodiment, the transformation function(s) used to calculate the modified statistical weights are predetermined based on imaging device specifications or scan parameters, as examples. Alternatively, the transformation function(s) may be selected based on analysis of an initial, first-pass reconstruction of the scanned image or a sinogram of the projection data. For example, if a metal trace is observed in the sinogram, the transformation function(s) may be tuned to generate modified statistical weights that minimize metal artifacts in the reconstruction.

The transformation functions set forth in Eqns. 11, 13, and 15, which are used in step 86 of technique 80 to calculate modified statistical weights for use in an iterative image reconstruction, use a threshold defined in the projection domain to divide the modified statistical weights into two regions. As one skilled in the art will recognize, the concepts set forth above may be expanded to further separate the statistical weights into any number of regions using multiple thresholds. According to various embodiments, the projection thresholds may be defined based on any number of factors, including, for example, scan parameters, IQ specifications, and the like. For each of the regions of the statistical weights, any of the transformation functions of Eqns. 6, 8, 9, 10, 11, 13, and 15 may be applied separately or in any combination thereof.

Figure 6:
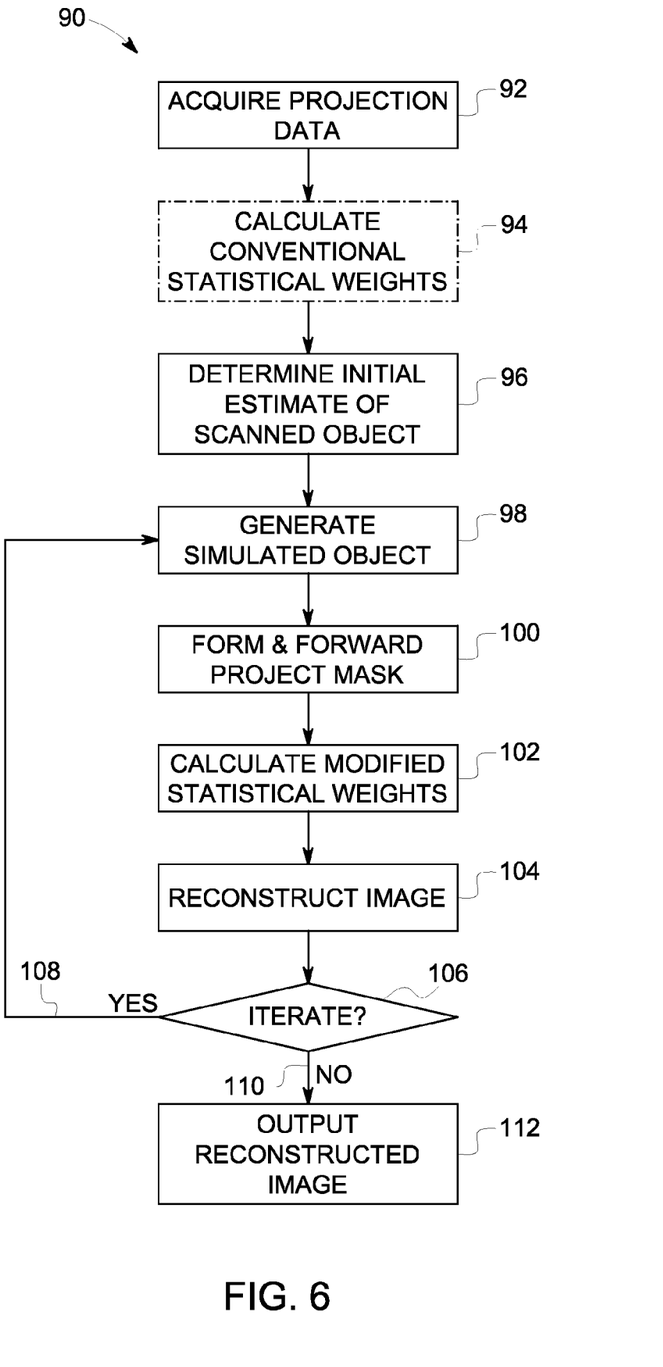
FIG. 6 is a flowchart illustrating a technique for reconstructing an image according to another embodiment of the invention.

Referring now to FIG. 6, an alternative image reconstruction technique 90 is disclosed that accounts for local material density within the scanned object, according to another embodiment. Dramatic changes in local material density within the object are one cause of the large dynamic range in conventional statistical weights. For example, in a human patient, lung tissue is significantly less attenuating that soft tissue as lung tissue has a density close to the density of air, whereas soft tissue has a density close to water. In transition regions between two tissue types, such as between lung tissue and liver or pancreas, or between the patient's skin and outside air, these large changes in local material density result in very large local gradients in the conventional statistical weights W. Since large local gradients in the conventional statistical weights W may lead to undesirable behavior during reconstruction and introduce artifacts, modified statistical weights may be calculated that correspond to a simulated object with fewer local changes in material density or smaller changes in local material density.

Technique 90 begins by acquiring a set of projection data from a scanned object at step 92, in a similar manner as described above with respect to step 82 of technique 80 (FIG. 5). At step 94 (shown in phantom), a set of conventional statistical weights is optionally calculated from the projection data, again in a similar manner as described with respect to step 82 of technique 80.

An initial image of the scanned object and its surroundings is reconstructed at step 96 to obtain a first estimate of the scanned object. The initial image may be reconstructed with or without the conventional statistical weights depending on the chosen initial reconstruction technique. According to various embodiments, technique 90 may utilize filtered back-projection reconstruction or a model-based iterative reconstruction (MBIR) technique to generate the initial image.

At step 98, technique 90 generates a simulation of projections of the scanned object by partitioning the initial image representing the scanned object and its surroundings into multiple density regions. According to one embodiment, technique 90 uses a histogramming technique to partition the initial image into N density regions $\{x_1, x_2, \ldots x_N\}$. A modified version $\tilde{x}_n$ of each density region n is then formed to simulate a more uniform object. As one example, $\tilde{x}_n$ is set to equal a constant, C, such as c=0 Hounsfield Units (HU) for water. Alternatively, $\tilde{x}_n$ is calculated according to:

$$\tilde{x}_n = x_n + C \quad \text{(Eqn. 17)},$$

in order to bring the elements of $\tilde{x}_n$ closer to those of another density region in the initial image. During set 98, technique 90 may calculate or assign a modified version of $\tilde{x}_n$ for one or more selected density regions, or all of the density regions, according to various embodiments.

In addition, the modified version $\tilde{x}_n$ of each density region n may be made more circular than the corresponding density region in the initial image to make the elements of the modified statistical weighting matrix $\tilde{W}$ uniform across all projection angles, for instance by adding a ring of simulated water to fill a convex shape around the real scanned object to form a simulated object boundary.

At step 100, a mask m is formed from a subtraction of the simulated object) $\tilde{x}$ and the real object x:

$$m = \tilde{x} - x \quad \text{(Eqn. 18)}.$$

Technique 90 forward projects the mask m to form an estimate of the difference in the projection measurements between the simulated object and the real object according to:

$$\Delta y = Am \quad \text{(Eqn. 19)}.$$

At step 102, modified statistical weights $\tilde{W}$ are calculated. According to various embodiments, the modified statistical weights $\tilde{W}$ may be calculated in accordance with one of the transformation functions set forth above, or using the nonlinear transformation of Eqn. 20 below, or any combination thereof, $$\tilde{W} = W \times e^{-\Delta y} \quad \text{(Eqn. 20)}.$$

A second image of the scanned object is reconstructed at step 104 using the modified statistical weights $\tilde{W}$. At step 106, technique 90 determines whether to perform another iteration in the MBIR reconstruction framework. In one exemplary embodiment, technique 90 determines whether to perform another iteration based on a comparison of the density regions determined during the current iteration and the density regions determined in the previous iteration. If another iteration is to be performed 108, technique 90 returns to step 98 and regenerates the simulated object. If another iteration is not to be performed 110, technique 90 proceeds to step 112 and outputs the reconstructed image. For example, technique 90 may display the reconstructed image to an operator or user on a display, such as display 42 illustrated in FIG. 1.

Figure 7:
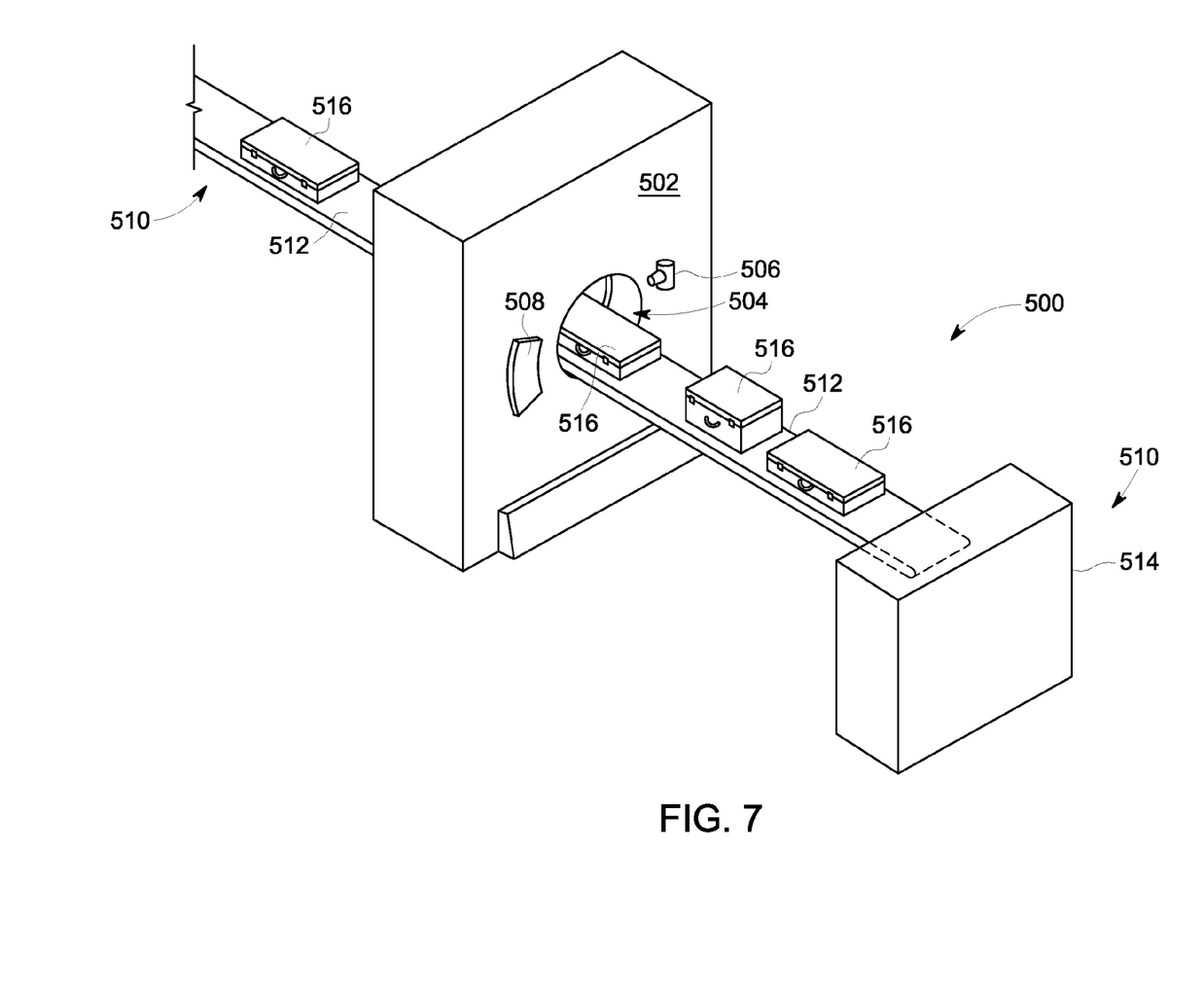
FIG. 7 is a pictorial view of a CT system for use with a non-invasive package inspection system.

Referring now to FIG. 7, package/baggage inspection system 500 includes a rotatable gantry 502 having an opening 504 therein through which packages or pieces of baggage may pass. The rotatable gantry 502 houses a high frequency electromagnetic energy source 506 as well as a detector assembly 508 having scintillator arrays comprised of scintillator cells similar to that shown in FIGS. 3 and 4. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc.

A technical contribution for the disclosed method and apparatus is that is provides for a computer implemented system and method of iterative image reconstruction for medical image data.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Therefore, in accordance with one embodiment, a non-transitory computer readable storage medium has stored thereon a computer program comprising instructions, which, when executed by a computer, cause the computer to acquire projection data from a scanned object, the set of projection data comprising a plurality of projection measurements. The instructions further cause the computer to calculate a set of modified statistical weights from the projection data, wherein a respective modified statistical weight of the set of modified statistical weights comprises a deviation from an inverse variance of a corresponding projection measurement of the projection data. The instructions also cause the computer to reconstruct an image of the scanned object using the set of modified statistical weights as coefficients in an iterative reconstruction algorithm.

In accordance with another embodiment, a method includes acquiring a projection dataset from an object using a medical imaging device, the projection dataset comprising a plurality of projection measurements representing attenuation of x-rays by the object. The method also includes generating a modified statistical weighting matrix comprising a plurality of weights that deviate from an inverse variance in the plurality of projection measurements and reconstructing an image of the object based on the modified statistical weighting matrix.

In accordance with yet another embodiment, an imaging system includes a rotatable gantry having an opening for receiving an object to be scanned and an x-ray source coupled to the rotatable gantry and configured to project x-rays through the opening. A generator is configured to energize the x-ray source to an energy level to generate x-rays corresponding to the energy level and a detector having pixels therein, the detector attached to the rotatable gantry and positioned to receive x-rays projected from the x-ray source. The imaging system also includes a computer programmed to access a CT projection dataset acquired from the object over a period of data acquisition, calculate a set of modified statistical weights for an iterative reconstruction algorithm using a scalar parameter tuned to differentiate projection rays of the CT projection dataset having differing attenuation values, and iteratively reconstruct the CT projection dataset using the set of modified statistical weights as coefficients in the iterative reconstruction algorithm.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A non-transitory computer readable storage medium having stored thereon a computer program comprising instructions, which, when executed by a computer, cause the computer to:
   acquire projection data from a scanned object, the set of projection data comprising a plurality of projection measurements;
   calculate a set of modified statistical weights from the projection data, wherein a respective modified statistical weight of the set of modified statistical weights comprises a deviation from an inverse variance of a corresponding projection measurement of the projection data; and
   reconstruct an image of the scanned object using the set of modified statistical weights as coefficients in an iterative reconstruction algorithm;
   wherein the instructions further cause the computer to:
      define a set of conventional statistical weights from the plurality of projection measurements, wherein a respective conventional statistical weight of the set of conventional statistical weights comprises an inverse variance of a respective projection measurement of the plurality of projection measurements; and
      apply a nonlinear transformation function to the set of conventional statistical weights to generate the set of modified statistical weights.

2. The computer readable storage medium of claim 1 wherein the deviation is independent of electronic noise.

3. The computer readable storage medium of claim 1 wherein the instructions cause the computer to generate a set of modified statistical weights that retains at least a portion of a dynamic range of the set of conventional statistical weights.

4. The computer readable storage medium of claim 1 wherein the instructions cause the computer to apply a power transformation to the set of conventional statistical weights to generate the set of modified statistical weights, the power transformation comprising a scalar exponent.

5. The computer readable storage medium of claim 1 wherein the instructions cause the computer to calculate the set of modified statistical weights to increase a relative difference between a projection measurement having a first signal-to-noise ratio (SNR) and a projection measurement having a second SNR.

6. The computer readable storage medium of claim 1 wherein the instructions cause the computer to calculate the set of modified statistical weights to decrease a relative difference between a projection measurement having a first SNR and a projection measurement having a second SNR.

7. The computer readable storage medium of claim 1 wherein the instructions cause the computer to:
   segment the plurality of projection measurements into a first region and a second region;
   generate a first set of modified statistical weights corresponding to the first region using a first transformation function; and
   generate a second set of modified statistical weights corresponding to the second region using a second transformation function.

8. The computer readable storage medium of claim 7 wherein the instructions cause the computer to generate a smooth transition between the first and second sets of modified statistical weights.

9. The computer readable storage medium of claim 1 wherein the instructions cause the computer to:
   perform an initial reconstruction of the scanned object;
   generate a simulation of projections of the scanned object based on the initial reconstruction;
   calculate a difference between acquired projections of the scanned object and the simulated projections; and
   generate the modified set of statistical weights using the calculated difference.

10. The computer readable storage medium of claim 9 wherein the instructions further cause the computer to:
    divide the initial reconstruction of the scanned object into a plurality of density regions, wherein each of the plurality of density regions comprises a respective range of density values;
    apply a modified density value to at least one of the plurality of density regions; and
    generate the simulated projections of the scanned object using the modified density value.

11. A method comprising:
    acquiring a projection dataset from an object using a medical imaging device, the projection dataset comprising a plurality of projection measurements representing attenuation of x-rays by the object;
    generating a modified statistical weighting matrix comprising a plurality of weights that deviate from an inverse variance in the plurality of projection measurements; and
    reconstructing an image of the object based on the modified statistical weighting matrix;

wherein, in generating the modified statistical weighting matrix, the method further comprises:
calculating a conventional statistical weighting matrix from the plurality of inverse variances; and
applying a nonlinear transformation function to the conventional statistical weighting matrix to generate the modified statistical weighting matrix.

12. The method of claim 11 further comprising:
calculating a plurality of inverse variances in the plurality of projection measurements using a computer processor; and
modifying the plurality of inverse variances to generate a modified statistical weighting matrix using the computer processor.

13. The method of claim 11 further comprising:
calculating a conventional statistical weighting matrix from the plurality of inverse variances; and
applying a transformation function to the conventional statistical weighting matrix to generate the modified statistical weighting matrix.

14. The method of claim 13 further comprising:
generating a sinogram from the projection dataset; and
defining the transformation function based on a feature of the sinogram.

15. The method of claim 13 further comprising:
using a first mathematical function to generate a first portion of the modified statistical weighting matrix corresponding to a first portion of the plurality of projection measurements; and
using a second mathematical function to generate a second portion of the modified statistical weighting matrix corresponding to a second portion of the plurality of projection measurements.

16. A non-transitory computer readable storage medium having stored thereon a computer program comprising instructions, which, when executed by a computer, cause the computer to:
acquire projection data from a scanned object, the set of projection data comprising a plurality of projection measurements;
calculate a set of modified statistical weights from the projection data, wherein a respective modified statistical weight of the set of modified statistical weights comprises a deviation from an inverse variance of a corresponding projection measurement of the projection data; and
reconstruct an image of the scanned object using the set of modified statistical weights as coefficients in an iterative reconstruction algorithm;
wherein the instructions further cause the computer to:
segment the plurality of projection measurements into a first region and a second region;
generate a first set of modified statistical weights corresponding to the first region using a first transformation function; and
generate a second set of modified statistical weights corresponding to the second region using a second transformation function.

17. The computer readable storage medium of claim 16 wherein the instructions cause the computer to generate a smooth transition between the first and second sets of modified statistical weights.

18. A non-transitory computer readable storage medium having stored thereon a computer program comprising instructions, which, when executed by a computer, cause the computer to:
acquire projection data from a scanned object, the set of projection data comprising a plurality of projection measurements;
calculate a set of modified statistical weights from the projection data, wherein a respective modified statistical weight of the set of modified statistical weights comprises a deviation from an inverse variance of a corresponding projection measurement of the projection data; and
reconstruct an image of the scanned object using the set of modified statistical weights as coefficients in an iterative reconstruction algorithm;
wherein the instructions further cause the computer to:
perform an initial reconstruction of the scanned object;
generate a simulation of projections of the scanned object based on the initial reconstruction;
calculate a difference between acquired projections of the scanned object and the simulated projections; and
generate the modified set of statistical weights using the calculated difference.

19. The computer readable storage medium of claim 18 wherein the instructions further cause the computer to:
divide the initial reconstruction of the scanned object into a plurality of density regions, wherein each of the plurality of density regions comprises a respective range of density values;
apply a modified density value to at least one of the plurality of density regions; and
generate the simulated projections of the scanned object using the modified density value.

20. A method comprising:
acquiring a projection dataset from an object using a medical imaging device, the projection dataset comprising a plurality of projection measurements representing attenuation of x-rays by the object;
generating a modified statistical weighting matrix comprising a plurality of weights that deviate from an inverse variance in the plurality of projection measurements; and
reconstructing an image of the object based on the modified statistical weighting matrix;
wherein, in generating the modified statistical weighting matrix, the method further comprises:
calculating a conventional statistical weighting matrix from the plurality of inverse variances; and
applying a transformation function to the conventional statistical weighting matrix to generate the modified statistical weighting matrix, wherein applying the transformation function comprises:
generating a sinogram from the projection dataset; and
defining the transformation function based on a feature of the sinogram.

21. A method comprising:
acquiring a projection dataset from an object using a medical imaging device, the projection dataset comprising a plurality of projection measurements representing attenuation of x-rays by the object;
generating a modified statistical weighting matrix comprising a plurality of weights that deviate from an inverse variance in the plurality of projection measurements; and
reconstructing an image of the object based on the modified statistical weighting matrix;

wherein, in generating the modified statistical weighting matrix, the method further comprises:
calculating a conventional statistical weighting matrix from the plurality of inverse variances;
applying a transformation function to the conventional statistical weighting matrix to generate the modified statistical weighting matrix, wherein applying the transformation function comprises:
using a first mathematical function to generate a first portion of the modified statistical weighting matrix corresponding to a first portion of the plurality of projection measurements; and
using a second mathematical function to generate a second portion of the modified statistical weighting matrix corresponding to a second portion of the plurality of projection measurements.

* * * * *